US009430022B2

(12) United States Patent
Kovachev et al.

(10) Patent No.: US 9,430,022 B2
(45) Date of Patent: Aug. 30, 2016

(54) METHOD AND APPARATUS FOR MODULAR POWER MANAGEMENT AND PROTECTION OF CRITICAL SERVICES IN AMBULATORY MEDICAL DEVICES

(75) Inventors: Boris P. Kovachev, Charlottesville, VA (US); Patrick T. Keith-Hynes, Charlottesville, VA (US); Marc D. Breton, Charlottesville, VA (US); Stephen D. Patek, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 159 days.

(21) Appl. No.: 14/128,811

(22) PCT Filed: Jun. 22, 2012

(86) PCT No.: PCT/US2012/043883
§ 371 (c)(1),
(2), (4) Date: Apr. 17, 2014

(87) PCT Pub. No.: WO2012/178113
PCT Pub. Date: Dec. 27, 2012

(65) Prior Publication Data
US 2014/0215239 A1 Jul. 31, 2014

Related U.S. Application Data

(60) Provisional application No. 61/500,551, filed on Jun. 23, 2011.

(51) Int. Cl.
*G06F 1/32* (2006.01)
*G06F 1/00* (2006.01)
(Continued)

(52) U.S. Cl.
CPC ......... *G06F 1/3212* (2013.01); *G06F 1/3206* (2013.01); *G06F 1/3234* (2013.01);
(Continued)

(58) Field of Classification Search
CPC .. G06F 1/3234; G06F 1/3287; G06F 1/3206; G06F 1/329; G06F 1/3212; G06F 9/34; G06F 9/3406; G06F 19/3406
USPC ........................................ 713/320, 340, 324
See application file for complete search history.

(56) References Cited

U.S. PATENT DOCUMENTS 5,936,383 A * 8/1999 Ng ........................ G01R 31/361
320/132
6,973,335 B2 12/2005 Ganton
(Continued)

FOREIGN PATENT DOCUMENTS

| EP | 1990887 A1 | 11/2008 |
|---|---|---|
| RU | 70730 | 2/2008 |
| RU | 98609 | 10/2010 |
| WO | 2006048838 A1 | 5/2006 |

OTHER PUBLICATIONS

Dan Clein, "What is Full Custom Layout Design?", Jun. 8, 2001, accessed at http://www.eetimes.com/document.asp?doc_id=1277368.*

*Primary Examiner* — Ji H Bae
(74) *Attorney, Agent, or Firm* — Vorys, Sater, Seymour and Pease LLP; Vincent M DeLuca; Robert J. Decker (57) ABSTRACT

Architecture and associated methods are provided for power management of ambulatory medical devices. The medical devices is described by a suite of services, each assigned a level of priority (from discretionary to critical), and the power management architecture allows use interchangeable control modules of various levels. A Power Safety Controller supervises the system to ensure appropriate preservation of critical services and provide warnings for low battery level. A Fidelity Controller ensures optimal allocation of power between the different services. A device supervision module estimates device characteristics which can be used by the other levels. The overall architecture ensures a safe and optimal management of services, and allows for a bottom-up deployment of the device.

12 Claims, 6 Drawing Sheets

(51) Int. Cl.
  *G06F 11/30* (2006.01)
  *H02J 1/14* (2006.01)
  *H02J 3/14* (2006.01)
  *H04W 52/02* (2009.01)
  *G06F 19/00* (2011.01)
  *G06F 9/34* (2006.01)
  *H02J 7/00* (2006.01)

(52) U.S. Cl.
  CPC  *H02J 1/14* (2013.01); *H02J 3/14* (2013.01); *H04W 52/0251* (2013.01); *H04W 52/0264* (2013.01); *G06F 1/329* (2013.01); *G06F 1/3287* (2013.01); *G06F 9/34* (2013.01); *G06F 19/3406* (2013.01); *H02J 2007/004* (2013.01)

(56) References Cited

U.S. PATENT DOCUMENTS

| | | |
|---|---|---|
| 7,725,094 B2 | 5/2010 | Chary |
| 2004/0235446 A1 | 11/2004 | Flaherty et al. |
| 2006/0279256 A1 | 12/2006 | Bletsas |
| 2008/0057894 A1 | 3/2008 | Aleksic et al. |
| 2010/0145643 A1 | 6/2010 | Katpelly et al. |
| 2010/0174928 A1* | 7/2010 | Borghetti ............ G06F 1/3203 713/320 |
| 2011/0072292 A1* | 3/2011 | Khawand ............ G06F 1/3203 713/340 |
| 2012/0131362 A1* | 5/2012 | Lee .................. H04W 52/0209 713/320 |
| 2012/0317432 A1* | 12/2012 | Assad .................. G06F 1/3212 713/340 |

* cited by examiner

METHOD AND APPARATUS FOR MODULAR POWER MANAGEMENT AND PROTECTION OF CRITICAL SERVICES IN AMBULATORY MEDICAL DEVICES

BACKGROUND OF THE INVENTION

The present invention relates generally to power management of mobile devices, which are powered by a battery power source. In particular, the invention relates to power management of a mobile device used to provide a medical service, such as measurement of blood glucose levels of a diabetic patient or other physiological monitoring of the patient/user, control of dosing devices such as perfusion pumps, intravenous fluid pumps, transmission of patient monitoring data to a remote center, etc.

Current mobile devices such as cellphones, tablet computers, personal digital assistants, laptop computers, etc. can be adapted to carry out a wide range of functions and perform a wide variety of services. Such devices can be enabled with software applications to carry out medical-related services such as the services mentioned above. Such devices are typically battery-powered and thus have a finite operating time before the battery goes dead and must be recharged. If the patient is not at a location where the device may be plugged into an electrical outlet, critical medical services may not be able to be provided. Such devices typically have the capability of performing multiple services simultaneously, such as cellphone services, email services, music player services, video player services, internet browsing, game playing, etc. If such a device is performing a critical medical service to a patient/user of the device while the device also is performing other services, battery power will be consumed at a faster rate. Consequently it would be desirable to have the ability to reduce or eliminate the power being consumed by non-critical or non-important services used on such a device, when the device also is being used to provide a critical medical service for the patient/user, and remaining battery power is approaching a low level.

SUMMARY OF THE INVENTION

An aspect of an embodiment of the present invention provides, among other things, architecture and associated methods for power management of ambulatory medical devices running on battery power. The services provided by the medical devices are described by a suite of services, wherein each service is assigned a level of priority (from discretionary to critical), and the power management architecture allows an interchangeable control module to be inserted at multiple control levels:
 a. Power Safety Control: supervises the system to ensure appropriate power management to maintain preservation of critical services and to provide adequate warnings to the user when remaining power is approaching critical levels.
 b. Fidelity Controller: ensures optimal allocation of power between the different services by optimizing performance levels of various services.
 c. Device Supervision: estimates device characteristics which can be used in the other layers.

The overall architecture ensures a safe and optimal management of services, and allows for a bottom-up deployment of the device.

In accordance with one embodiment, a power management system for managing power consumption of a battery-operated device configured to provide a plurality of services includes a device characteristics estimation module configured to receive a battery level of said device, at least one parameter of a user of the device, and the services being provided by the device, said device characteristics estimation module being further configured to construct time profiles encoding a probability of at least one of said battery level, user parameter, and services being provided having certain values at each of a number of time segment k; a fidelity controller module configured to receive said time profiles from said device characteristics estimation module and said battery level, and to set a fidelity policy $u(k)$ for each time segment k, said fidelity policy defining a level of fidelity for each service; a power controller module configured to receive said fidelity policy $u(k)$ and said battery level, to compute an amount of time remaining before battery exhaustion under said battery level and a mode of operation having a predefine power consumption rate, and to take a predetermined action based on the computed amount of time remaining with respect to at least one preset threshold; and a device service regulator module for regulating access of said services to resources of said device for performing said services, in accordance with a predetermined action communicated from the power controller module.

According to another embodiment, a computer-implemented method for managing power consumption of a battery-operated device configured to provide a plurality of services includes performing by a processor: receiving a battery level of said device, at least one parameter of a user of the device, and the services being provided by the device, constructing time profiles encoding a probability of at least one of said battery level, user parameter, and services being provided having certain values at each of a number of time segment k; setting a fidelity policy $u(k)$ for each time segment k, said fidelity policy defining a level of fidelity for each service, based on said time profiles and battery level; computing, based on said time profiles, an amount of time remaining before battery exhaustion under said battery level and a mode of operation having a predefine power consumption rate, and taking a predetermined action based on the computed amount of time remaining with respect to at least one preset threshold; and regulating access of said services to resources of said device for performing said services, in accordance with said predetermined action.

According to yet another embodiment, a non-transitory computer-readable storage medium having stored thereon computer-executable instructions, with respect to managing power consumption of a battery-operated device configured to provide a plurality of services, causing a computer to perform: receiving a battery level of said device, at least one parameter of a user of the device, and the services being provided by the device, constructing time profiles encoding a probability of at least one of said battery level, user parameter, and services being provided having certain values at each of a number of time segment k; setting a fidelity policy $u(k)$ for each time segment k, said fidelity policy defining a level of fidelity for each service, based on said time profiles and battery level; computing, based on said time profiles, an amount of time remaining before battery exhaustion under said battery level and a mode of operation having a predefine power consumption rate, and taking a predetermined action based on the computed amount of time remaining with respect to at least one preset threshold; and regulating access of said services to resources of said device for performing said services, in accordance with said predetermined action.

DETAILED DESCRIPTION OF THE INVENTION

Formulation:

let $\vec{a} = \{a_i | 1 = 1 \ldots n\}$ be the set of installed activities or services on an ambulatory or mobile device, and $\{u_j = [u_{1,j}, u_{2,j}, \ldots, u_{n,j}] | j = 1 \ldots m\}$ be the set of allowed fidelity policies for each activity or service, wherein a fidelity policy is associated with a particular power consumption rate. We then propose that for each time segment k, the power remaining $x(k+1)$ can be modeled as $$x(k+1) = x(k) - \omega(k) \text{ where} \quad (1.1)$$

$$\omega(k) = \sum_{i=1}^{n} f_{i, u_{i,j}(k)}(Ia_i(k))$$

is the power consumption at stage k, with $f_{i, u_{i,j}(k)}(Ia_i(k))$ being the power consumption associated with activity $a_i$, under the fidelity policy $u_j(k)$.

Therefore the power consumption can be seen as a stochastic process governed by the binomial probability distributions $P(Ia_i(k)=1)$ and the chosen set of fidelity policies at each time segment k.

Architecture

An aspect of an embodiment of the present invention is organized around, for example, a specific architecture of control modules, each controlling one aspect of the power management problem. This architecture allows for the disambiguation of the control objective (usability versus critical service functionality versus battery life) and its modularity ensures that regardless of the optimal power management strategy chosen, critical services are protected and the device is capable of performing its core medical functionalities.

Figure 1:
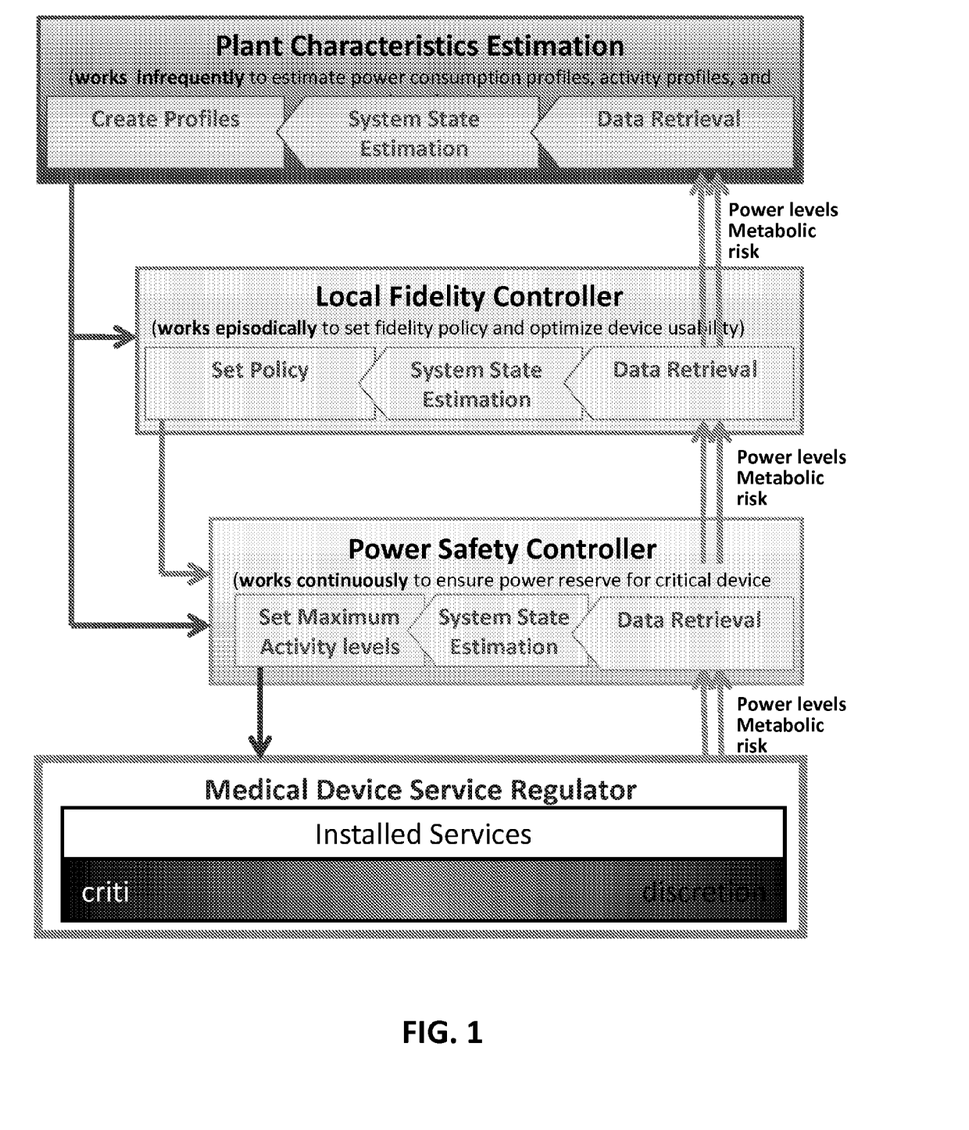
FIG. 1 is a block diagram showing the various power management control modules and their relationships to each other, in accordance with an embodiment of the invention.

Referring to FIG. 1, the architecture contains control modules at 4 levels of increasing abstraction:

a. The Medical Device Services Regulator (MDSR), which controls the resource access of all installed services on the device, wherein service is a set of self-contained software commands designed to execute a specific action. The MDSR is responsible for translating the set of policies generated by the power controller into resource access for the services, potentially shutting down superfluous or non-critical services. The installed services are categorized into a plurality of defined priority levels from critical to discretionary. The MDSR also provides power level and patient risk information to the Power Safety Controller (PSC).

b. The Power Safety Controller (PSC), which ensures maximum availability of critical services, i.e. services necessary for the functioning of the medical device. This module analyzes the amount of remaining power as communicated from the MDSR, estimates the amount of operating time remaining, and based on the estimate may decide to override policies set at higher levels to ensure priority of critical services over all others when the battery level gets low. In addition the PSC is responsible for warning the user of power preservation schemes, and alerting the user of an imminent power shutdown.

c. The Local Fidelity Controller (LFC), which optimizes the fidelity levels for each of the activities. A fidelity level defines a level of operation for a service, and corresponds with a certain power consumption rate. The combination of all fidelity levels defines the current fidelity policy.

d. The Plant Characteristics Estimator (PCE), which observes the operating state of the device and estimates time-dependent profiles for activities usage, power consumption for activities at specific fidelity levels, and patient's risk.

Each level of the architecture runs at a potentially different frequency, with the MDSR being run continuously, the PSC being run continuously or frequently, the LFC being run intermittently or episodically, and the PCE being run infrequently or rarely.

Power Safety Controller (PSC)

Overall Design

The power safety controller (PSC) computes the amount of time remaining before battery exhaustion under the current battery level and a "critical services only" mode of functioning or power consumption rate.

Figure 2:
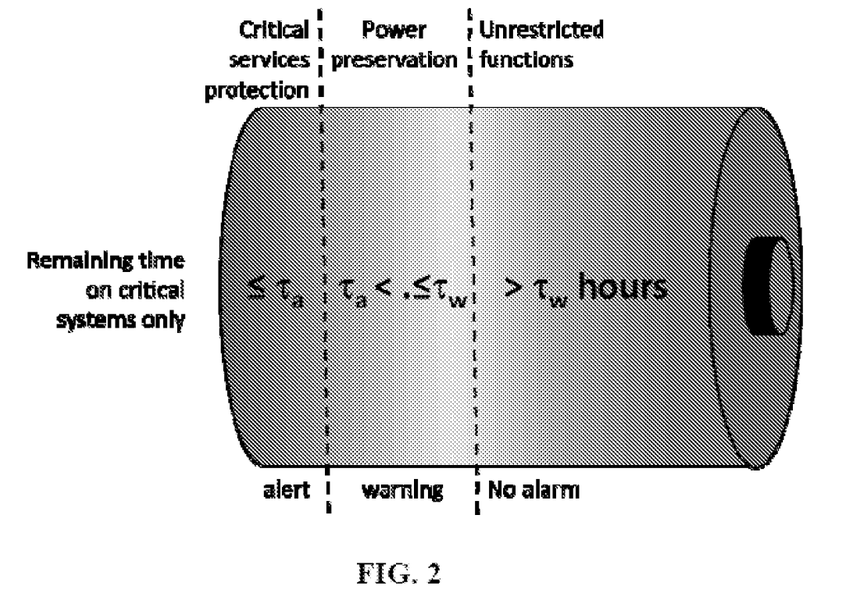
FIG. 2 is a diagram showing one example of a power management control and warning scheme in accordance with an embodiment of the invention.

Based on this assessment of the remaining functional time (rft) and internally set thresholds for a warning ($\tau_w$) and an alert ($\tau_a$), the system takes one of three actions, as shown in FIG. 2:

if rft>$\tau_w$, the PSC passes through the current power allocation policy (either preset or output from the local fidelity controller) to the medical device service regulator (green light);

if rft≤$\tau_w$ and rft>$\tau_a$ the PSC preserves power by:
  stopping discretionary services,
  lowering fidelity levels of important and critical services, and
  warning the user of approaching battery depletion and activation of the power preservation mode (orange light);

if rft<$\tau_a$, the PSC:
  stops all non-critical services,
  lowers the fidelity levels of the critical services,
  prepares the system for shutdown (data dump, deactivation of peripheral devices, etc.), and
  outputs an alarm alerting the user of imminent battery depletion (red light).

Estimation of the Remaining Functional Time

Figure 3:
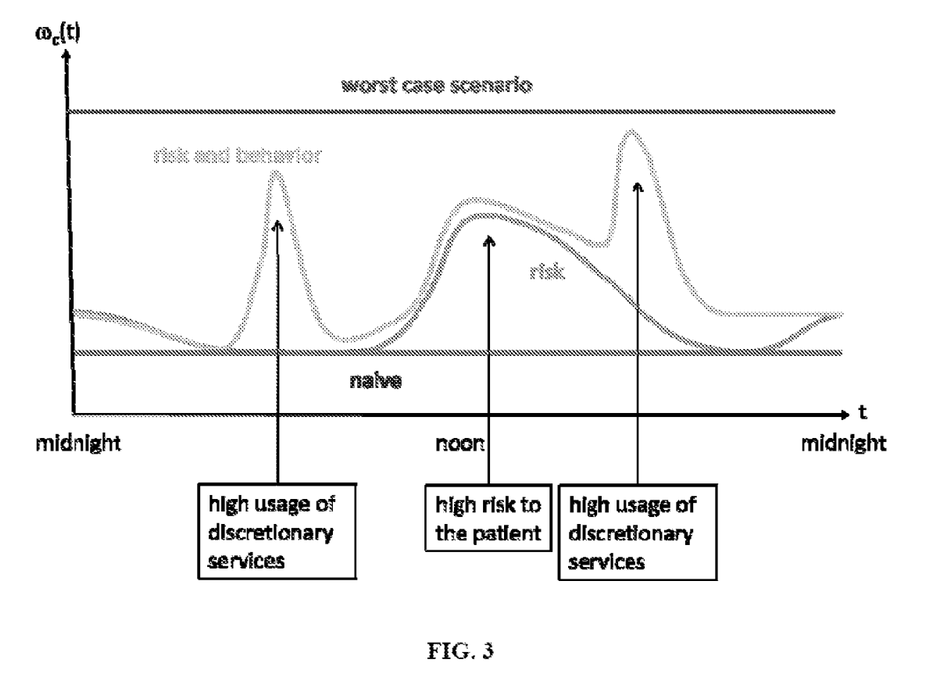
FIG. 3 is a graph illustrating various power consumption scenarios for use in estimating remaining functional time for a device in accordance with an embodiment of the invention.
Figure 4:
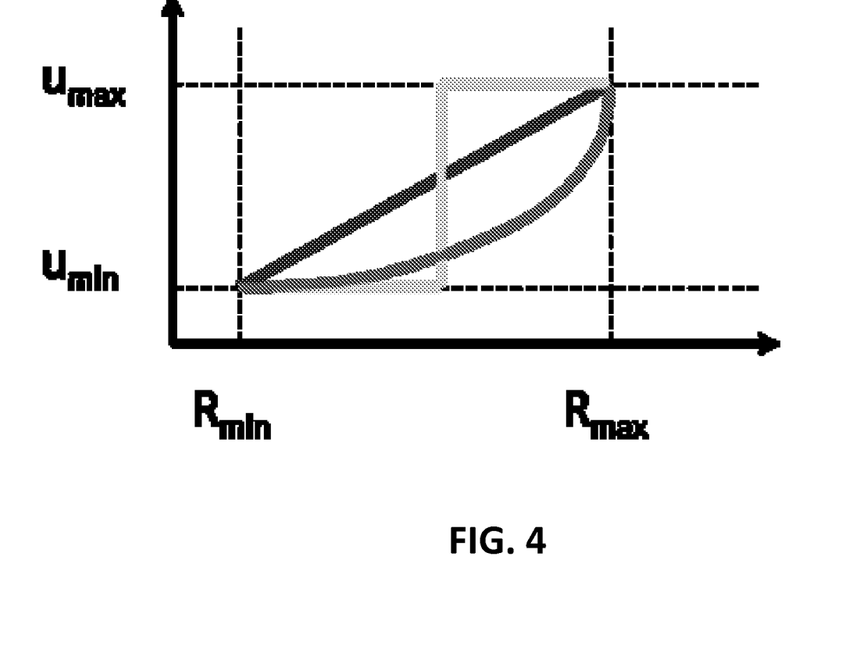
FIG. 4 is a graph illustrating various functions of fidelity level versus patient risk, which can be used to determine fidelity levels for critical services as a function of patient risk.

The PSC can function with a variety of Remaining Functional Time (RFT) estimators. As shown in FIG. 3, four classes of RFT estimator range from the least conservative (naïve) to the most conservative (worst case scenario). While classes 1 and 4 are limit cases (naïve and worst case scenario) and do not request additional input from the known consumption and battery level, cases 2 and 3 require an estimation (or a profile over time) of the risk to the patient, and of the service activities being used. In FIG. 4, we present an example risk profile where the patient is particularly at risk in the early afternoon, and an example behavior profile where the patient uses her device during her commute to and from work for discretionary activities (e.g. internet, media, games, emails, etc.)

Naïve RFT Estimation

Using the formulation proposed above, a naïe estimation of the RFT is given by a simple accounting formula, where x(k) is the remaining battery life in hours and co is the consumption by hour, and $u_{min}$ is the policy imposing the lowest fidelity before shut off for all activities:

$$rft(k) = x(k)/w_c(k) \text{ where}$$

$$\begin{cases} w_c(k) = \sum_{i=1}^{n} f_{i,u_{min}}(I_c a_i) \\ I_c a_i = \begin{cases} 1 & \text{if } a_i \text{ is critical} \\ 0 & \text{otherwise} \end{cases} \end{cases} \quad (1.2)$$

Risk Informed RFT Estimation

Risk informed RFT estimation makes use of the estimated medical risk to the patient in accordance with the risk profile, to estimate the future policies per time segment k: i.e. if the patient's risk is high, the fidelity of critical services will not be lowered, while if the patient is safe it is appropriate to lower the fidelity of critical services.

This can be done either by using the risk profile generated in the upper layer of the architecture, or by extrapolating the risk at its current values to the time segment under consideration.

In both cases the RFT estimate is $$rft(k) = \operatorname{argmin} \left| x(k) - \sum_{t=1}^{\tau} \omega_c(k+t) \right| \quad (1.3)$$

where $$\begin{cases} \omega_c(k) = \sum_{i=1}^{n} f_{i,u(k)}(I_c a_i) \\ I_c a_i = \begin{cases} 1 & \text{if } a_i \text{ is critical} \\ 0 & \text{otherwise} \end{cases} \\ u(k) = g(R(k)) \end{cases}$$

Here we see that the fidelity level of the critical services is dependent on the estimated patient's risk over time through the function g. G can be of many forms as shown in FIG. 4, but the key characteristic is that during risky periods the fidelity of the critical services is increased.

Behaviorally Informed RFT Estimation

Figure 5:
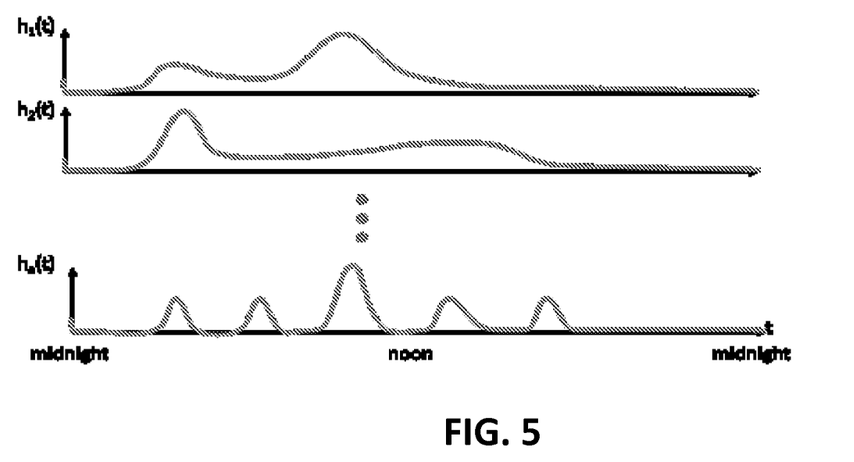
FIG. 5 is a graph illustrating examples of probabilities of activities or services being used during various time segments of the day, used to estimate remaining functional time of a device in accordance with an embodiment of the invention.

In addition to the risk-based assessment of RFT, it is interesting to look at behavioral profiles to estimate power consumption. Here we think in terms especially of multi-use medical devices (such as pump control or sensor monitoring from cell phones or tablet computers). As the device is used for many more things than its critical services (e.g. medical uses) it is important to account for the variability of the patient's use of these discretionary functions. The upper layer of the architecture (Plant Characteristics Estimation) is designed to generate profiles of use for all activities, therefore enabling accounting for "expected use" in the computation of RFT, as follows:

$$rft(k) = \operatorname{argmin} \left| x(k) - \sum_{t=1}^{\tau} \omega_c(k+t) \right| \quad (1.4)$$

where $$\begin{cases} \omega_c(k) = \sum_{i=1}^{n} h_i(k) f_{i,u(k)}(1) \\ u(k) = g(R(k)) \end{cases}$$

where $h_i(k)$ is the probability of activity $a_i$ to be used during time segment k. Examples of such probability curves are shown in FIG. 5.

Worst Case Scenario RFT Estimation

Using the formulation proposed above, a worst case scenario estimation of the RFT is given by a simple accounting formula, where x(k) is the remaining battery life in hours, co is the consumption by hour, and $u_{max}$ is the policy allowing all services to function at maximum fidelity:

$$rft(k) = x(k)/w_c(k) \quad (1.5)$$

where $$w_c(k) = \sum_{i=1}^{n} f_{i,u_{max}}(1)$$

Local Fidelity Controller

The local fidelity controller (LFC) sets the policy u(k) for each time segment k. The policy defines the level of fidelity for each activity and can be computed any number of ways. The details of this computation are not part of this invention and thus will not be discussed herein. Such details can be devised by known methods that are not specific to medical devices. The important consideration is that the system makes available to the LFC at each time segment k the battery level, the estimated risk to the patient, and the activities or services being used by the device. Compatibility with the overall system is achieved by ensuring that policies computed through the LFC are translatable by the MDSR.

Plant Characteristics Estimation

The PCE receives from the architecture at each time segment k:
  battery level,
  the estimated risk to the patient, and
  the activities being used by the device.

For each input it constructs a time profile, which encodes the probability of each variable having certain values at each stage k. Such profiles can be described over any time span (e.g. one hour, 24 h, 1 week,) or even be specific to type of days/week (work, vacation, weekend, etc.)

Figure 6:
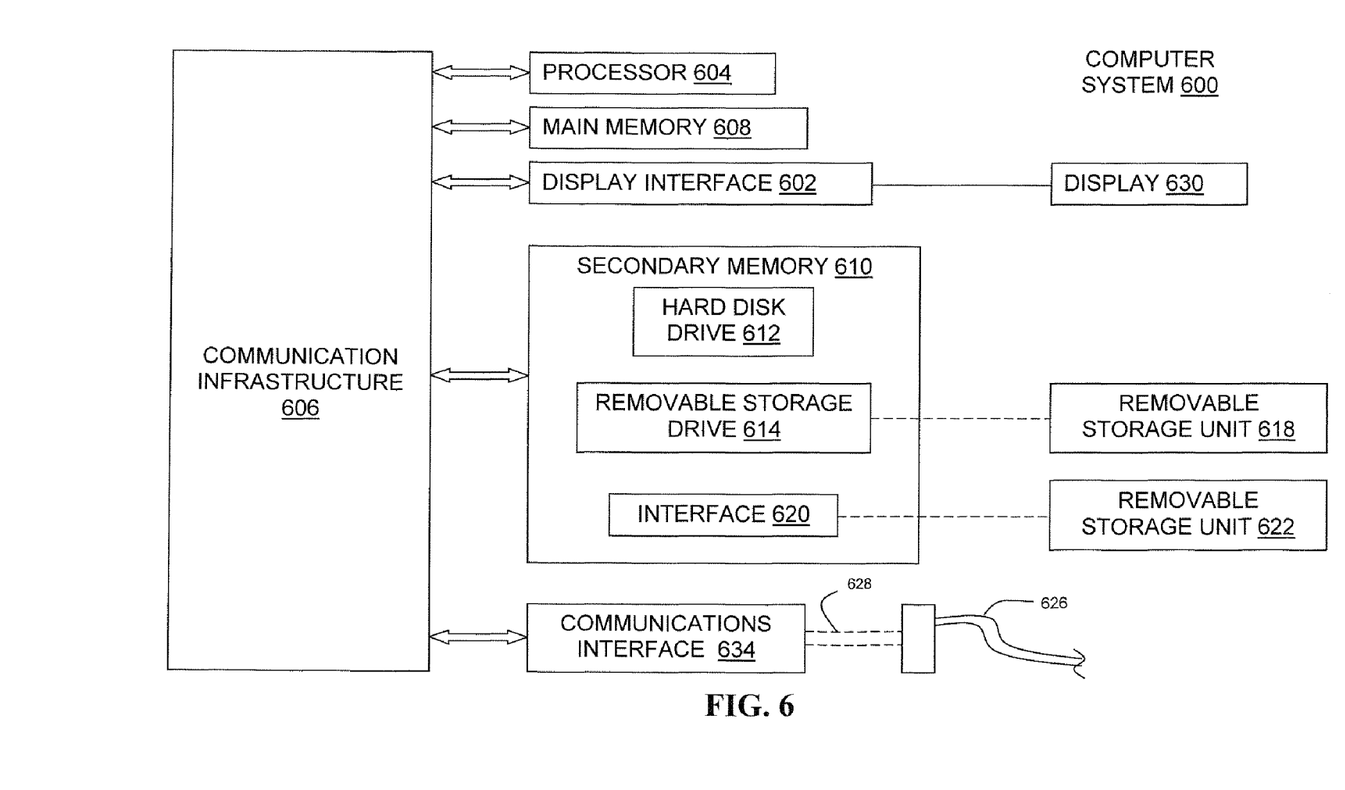
FIG. 6 is a block diagram of an exemplary computer system for implementation of an embodiment of the invention.

Commonly available probability distribution estimators can be used to construct:
  Activity Profiles,
  Metabolic Risk Profiles
  Activity Specific Consumption Profile Turning to FIG. 6, FIG. 6 is a functional block diagram for a computer system 600 for implementation of an exemplary embodiment or portion of an embodiment of present invention. For example, a method or system of an embodiment of the present invention may be implemented using hardware, software or a combination thereof and may be implemented in one or more computer systems or other processing systems, such as personal digit assistants (PDAs) equipped with adequate memory and processing capabilities. In an example embodiment, the invention was implemented in software running on a general purpose computer 60 as illustrated in FIG. 6. The computer system 600 may include one or more processors, such as processor 604. The Processor 604 is connected to a communication infrastructure 606 (e.g., a communications bus, cross-over bar, or network). The computer system 600 may include a display interface 602 that forwards graphics, text, and/or other data from the communication infrastructure 606 (or from a frame buffer not shown) for display on the display unit 630. Display unit 630 may be digital and/or analog.

The computer system 600 may also include a main memory 608, preferably random access memory (RAM), and may also include a secondary memory 610. The secondary memory 610 may include, for example, a hard disk drive 612 and/or a removable storage drive 614, representing a floppy disk drive, a magnetic tape drive, an optical disk drive, a flash memory, etc. The removable storage drive 614 reads from and/or writes to a removable storage unit 618 in a well known manner. Removable storage unit 618, represents a floppy disk, magnetic tape, optical disk, etc. which is read by and written to by removable storage drive 614. As will be appreciated, the removable storage unit 618 includes a computer usable storage medium having stored therein computer software and/or data.

In alternative embodiments, secondary memory 610 may include other means for allowing computer programs or other instructions to be loaded into computer system 600. Such means may include, for example, a removable storage unit 622 and an interface 620. Examples of such removable storage units/interfaces include a program cartridge and cartridge interface (such as that found in video game devices), a removable memory chip (such as a ROM, PROM, EPROM or EEPROM) and associated socket, and other removable storage units 622 and interfaces 620 which allow software and data to be transferred from the removable storage unit 622 to computer system 600.

The computer system 600 may also include a communications interface 624. Communications interface 124 allows software and data to be transferred between computer system 600 and external devices. Examples of communications interface 624 may include a modem, a network interface (such as an Ethernet card), a communications port (e.g., serial or parallel, etc.), a PCMCIA slot and card, a modem, etc. Software and data transferred via communications interface 624 are in the form of signals 628 which may be electronic, electromagnetic, optical or other signals capable of being received by communications interface 624. Signals 628 are provided to communications interface 624 via a communications path (i.e., channel) 626. Channel 626 (or any other communication means or channel disclosed herein) carries signals 628 and may be implemented using wire or cable, fiber optics, blue tooth, a phone line, a cellular phone link, an RF link, an infrared link, wireless link or connection and other communications channels.

In this document, the terms "computer program medium" and "computer usable medium" are used to generally refer to media or medium such as various software, firmware, disks, drives, removable storage drive 614, a hard disk installed in hard disk drive 612, and signals 628. These computer program products ("computer program medium" and "computer usable medium") are means for providing software to computer system 600. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) are may be stored in main memory 608 and/or secondary memory 610. Computer programs may also be received via communications interface 624. Such computer programs, when executed, enable computer system 600 to perform the features of the present invention as discussed herein. In particular, the computer programs, when executed, enable processor 604 to perform the functions of the present invention. Accordingly, such computer programs represent controllers of computer system 600.

In an embodiment where the invention is implemented using software, the software may be stored in a computer program product and loaded into computer system 600 using removable storage drive 614, hard drive 612 or communications interface 624. The control logic (software or computer program logic), when executed by the processor 604, causes the processor 604 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in SPSS control language or C++ programming language, but could be implemented in other various programs, computer simulation and computer-aided design, computer simulation environment, MATLAB, or any other software platform or program, windows interface or operating system (or other operating system) or other programs known or available to those skilled in the art.

The invention having been thus disclosed, it will be apparent to those skilled in the art that the same may be implemented in many ways without departing from the spirit and scope of the invention. Any and all such variations are intended to be included within the scope of the following claims.

REFERENCES

The devices, systems, computer program products, and methods of various embodiments of the invention disclosed herein may utilize aspects disclosed in the following references, applications, publications and patents and which are hereby incorporated by reference herein in their entirety:
1. European Patent Application Publication No. EP 1 737 099 A1, Veselic, et al., "Power Management Systems and Methods for a Mobile Device", Dec. 27, 2006.
2. International Patent Application Publication No. WO 2008/070481 A1, Fadell, A., "Power Consumption Management for Functional Preservation in a Battery-Powered Electronic Device", Jun. 12, 2008.
3. European Patent Application Publication No. EP 1 990 887 A1, Nebon, J., "A Power Management Unit for Battery-Operated Devices", Nov. 12, 2008.

4. International Patent Application Publication No. WO 2006/048838 A1, Maack, H., "Wireless Battery Status Management for Medical Devices", May 11, 2006.

The invention claimed is:

1. A computer-implemented method for managing power consumption of a battery-operated device configured to provide a plurality of services, comprising, performing by a processor:
  receiving a battery level of said device, at least one parameter of a user of the device, and the services being provided by the device, constructing time profiles encoding a probability of at least one of said battery level, user parameter, and services being provided having certain values at each of a number of time segments k;
  setting a fidelity policy u(k) for each time segment k, said fidelity policy defining a level of fidelity for each service, based on said time profiles and battery level;
  computing, based on said time profiles, an amount of time remaining before battery exhaustion under said battery level and a mode of operation having a predefine power consumption rate, and taking a predetermined action based on the computed amount of time remaining with respect to at least one preset threshold; and
  regulating access of said services to resources of said device for performing said services, in accordance with said predetermined action.

2. The method of claim 1, wherein at least one of said services is a critical service being provided to said user, said at least one parameter is a risk level of said user with respect to said critical service, said amount of time remaining is computed based on said risk level of said user, and said predetermined action causes maximizing availability of said critical service to said user.

3. The method of claim 2, wherein said amount of time remaining is computed by the equation:

$$rft(k) = x(k)/w_c(k)$$

where $$\begin{cases} w_c(k) = \sum_{i=1}^{n} f_{i,u_{min}}(I_c a_i) \\ I_c a_i = \begin{cases} 1 & \text{if } a_i \text{ is critical} \\ 0 & \text{otherwise} \end{cases} \end{cases}$$

where rft(k) is the amount of time remaining at time segment k, x(k) is remaining battery life, and $a_i$ is a service being used.

4. The method of claim 2, wherein said amount of time remaining is computed by the equation:

$$rft(k) = \operatorname{argmin} \left| x(k) - \sum_{t=1}^{\tau} \omega_c(k+t) \right|$$

where $$\begin{cases} \omega_c(k) = \sum_{i=1}^{n} f_{i,u(k)}(I_c a_i) \\ I_c a_i = \begin{cases} 1 & \text{if } a_i \text{ is critical} \\ 0 & \text{otherwise} \end{cases} \\ u(k) = g(R(k)) \end{cases}$$

where rft(k) is the amount of time remaining at time segment k, x(k) is remaining battery life, ω is power consumption rate, R(k) is a function of said risk of said user, and $a_i$ is a service being used.

5. The method of claim 2, wherein said amount of time remaining is computed by the equation:

$$rft(k) = \operatorname{argmin} \left| x(k) - \sum_{t=1}^{\tau} \omega_c(k+t) \right|$$

where $$\begin{cases} \omega_c(k) = \sum_{i=1}^{n} h_i(k) f_{i,u(k)}(1) \\ u(k) = g(R(k)) \end{cases}$$

where rft(k) is the amount of time remaining at time segment k, x(k) is remaining battery life, ω is power consumption rate, R(k) is a function of said risk of said user, $a_i$ is a service, and $h_i(k)$ is a probability of service $a_i$ to be used during time segment k.

6. The method of claim 2, wherein said amount of time remaining is computed by the equation:

$$rft(k) = x(k)/w_c(k)$$

where $$w_c(k) = \sum_{i=1}^{n} f_{i,u_{max}}(1)$$

where rft(k) is the amount of time remaining at time segment k, and x(k) is remaining battery life.

7. A non-transitory computer-readable storage medium having stored thereon computer-executable instructions, with respect to managing power consumption of a battery-operated device configured to provide a plurality of services, causing a computer to perform:
  receiving a battery level of said device, at least one parameter of a user of the device, and the services being provided by the device, constructing time profiles encoding a probability of at least one of said battery level, user parameter, and services being provided having certain values at each of a number of time segments k;
  setting a fidelity policy u(k) for each time segment k, said fidelity policy defining a level of fidelity for each service, based on said time profiles and battery level;
  computing, based on said time profiles, an amount of time remaining before battery exhaustion under said battery level and a mode of operation having a predefine power consumption rate, and taking a predetermined action based on the computed amount of time remaining with respect to at least one preset threshold; and
  regulating access of said services to resources of said device for performing said services, in accordance with said predetermined action.

8. The non-transitory computer-readable storage medium of claim 7, wherein at least one of said services is a critical service being provided to said user, said at least one parameter is a risk level of said user with respect to said critical service, said amount of time remaining is computed based on said risk level of said user, and said predetermined action causes maximizing availability of said critical service to said user.

9. The non-transitory computer-readable storage medium of claim 8, wherein said amount of time remaining is computed by the equation:

$$rft(k) = x(k)/w_c(k)$$

where $$\begin{cases} w_c(k) = \sum_{i=1}^{n} f_{i,u_{min}}(I_c a_i) \\ I_c a_i = \begin{cases} 1 & \text{if } a_i \text{ is critical} \\ 0 & \text{otherwise} \end{cases} \end{cases}$$

where rft(k) is the amount of time remaining at time segment k, x(k) is remaining battery life, and $a_i$ is a service being used.

10. The non-transitory computer-readable storage medium of claim 8, wherein said amount of time remaining is computed by the equation:

$$rft(k) = \operatorname{argmin} \left| x(k) - \sum_{t=1}^{\tau} \omega_c(k+t) \right|$$

where $$\begin{cases} \omega_c(k) = \sum_{i=1}^{n} f_{i,u(k)}(I_c a_i) \\ I_c a_i = \begin{cases} 1 & \text{if } a_i \text{ is critical} \\ 0 & \text{otherwise} \end{cases} \\ u(k) = g(R(k)) \end{cases}$$

where rft(k) is the amount of time remaining at time segment k, x(k) is remaining battery life, ω is power consumption rate, R(k) is a function of said risk of said user, and $a_i$ is a service being used.

11. The non-transitory computer-readable storage medium of claim 8, wherein said amount of time remaining is computed by the equation:

$$rft(k) = \operatorname{argmin} \left| x(k) - \sum_{t=1}^{\tau} \omega_c(k+t) \right|$$

where $$\begin{cases} \omega_c(k) = \sum_{i=1}^{n} h_i(k) f_{i,u(k)}(1) \\ u(k) = g(R(k)) \end{cases}$$

where rft(k) is the amount of time remaining at time segment k, x(k) is remaining battery life, ω is power consumption rate, R(k) is a function of said risk of said user, $a_i$ is a service, and $h_i(k)$ is a probability of service $a_i$ to be used during time segment k.

12. The non-transitory computer-readable storage medium of claim 8, wherein said amount of time remaining is computed by the equation:

$$rft(k) = x(k)/w_c(k)$$

where $$w_c(k) = \sum_{i=1}^{n} f_{i,u_{max}}(1)$$

where rft(k) is the amount of time remaining at time segment k, and x(k) is remaining battery life.

* * * * *